US008679077B2

(12) United States Patent
Elish et al.

(10) Patent No.: US 8,679,077 B2
(45) Date of Patent: Mar. 25, 2014

(54) SYSTEM AND METHOD FOR DELIVERING MOISTURIZING LIQUID TO LIPS OF A SUBJECT

(75) Inventors: Oded Elish, Kiriat-Tivon (IL); Ehud Nagler, Kiriat-Tivon (IL); Gilad Heftman, Ein-Gev (IL)

(73) Assignee: IMD Tech Ltd., Kiriat-Tivon (IL)

( * ) Notice: Subject to any disclaimer, the term of this patent is extended or adjusted under 35 U.S.C. 154(b) by 331 days.

(21) Appl. No.: 12/866,291

(22) PCT Filed: Feb. 11, 2009

(86) PCT No.: PCT/IB2009/050559

§ 371 (c)(1), (2), (4) Date: Aug. 5, 2010

(87) PCT Pub. No.: WO2009/101585

PCT Pub. Date: Aug. 20, 2009

(65) Prior Publication Data

US 2010/0324508 A1 Dec. 23, 2010

Related U.S. Application Data

(60) Provisional application No. 61/027,503, filed on Feb. 11, 2008.

(51) Int. Cl.
*A61M 35/00* (2006.01)

(52) U.S. Cl.
USPC ........ 604/290; 604/19; 604/289; 128/200.16; 128/200.21

(58) Field of Classification Search
None
See application file for complete search history.

(56) References Cited

U.S. PATENT DOCUMENTS

| | | | | | |
|---|---|---|---|---|---|
| 4,679,551 | A * | 7/1987 | Anthony | 601/160 |
| 4,838,882 | A | 6/1989 | Molinoff | |
| 4,893,956 | A * | 1/1990 | Wojcik et al. | 401/130 |
| 4,917,674 | A | 4/1990 | Molinoff | |
| 5,055,108 | A | 10/1991 | Jenkins | |
| 5,062,795 | A | 11/1991 | Woog | |
| 5,927,661 | A * | 7/1999 | Tinsley et al. | 248/102 |
| 6,053,898 | A * | 4/2000 | Ostrow | 604/310 |
| 6,082,583 | A * | 7/2000 | Bussell et al. | 222/1 |
| 6,450,166 | B1 | 9/2002 | McDonald | |
| 6,536,423 | B2 * | 3/2003 | Conway | 128/200.14 |
| 6,691,706 | B2 * | 2/2004 | Ives | 128/204.13 |
| 7,416,358 | B2 | 8/2008 | Legendre | |
| 2003/0150885 | A1 * | 8/2003 | Dunne | 222/402.24 |
| 2004/0258457 | A1 * | 12/2004 | Legendre | 401/205 |
| 2005/0066463 | A1 * | 3/2005 | Brunner | 15/167.2 |
| 2008/0019758 | A1 * | 1/2008 | Mallardi, III | 401/6 |

FOREIGN PATENT DOCUMENTS

EP 1810712 7/2007

* cited by examiner

*Primary Examiner* — (Jackie) Tan-Uyen T. Ho
*Assistant Examiner* — Eric Bryant
(74) *Attorney, Agent, or Firm* — Mark M. Friedman

(57) ABSTRACT

A system for delivering moisturizing liquid to the lips of a subject includes an applicator for applying the moisturizing liquid to the lips supported by a support structure so that at least a part of applicator is deployed so as to engage a recess between the lips of subject without obstructing contact between the subject's upper and lower lips. The proximity of the applicator to the lips allows the use of simple contact-based implementations of the applicator. At the same time, disruption of speech and other normal oral movement is minimized by avoiding any obstruction to contact between the lips.

17 Claims, 8 Drawing Sheets

20
22
14

16

16
24
12
10
26

14
16
18

SYSTEM AND METHOD FOR DELIVERING MOISTURIZING LIQUID TO LIPS OF A SUBJECT

RELATED APPLICATIONS

This patent application is a U.S. National Phase Application of PCT/IB2009/050559 filed on Feb. 11, 2009, which claims priority of U.S. Patent Application No. 61/027,503 filed Feb. 11, 2008, the contents of which are incorporated herein by reference.

FIELD AND BACKGROUND OF THE INVENTION

The present invention relates to a system and method for delivering moisturizing liquid to the lips of a subject suffering from dry lips, for example, after undergoing surgery.

It is common for patients recovering from surgery, particularly during recovery from general anesthesia, to suffer from dry or cracked lips. In some cases, this problem may persist for several days after surgery. During the recovery period, the patient is typically allowed only very limited amounts of water or cracked ice due to the risk of inducing vomiting. The discomfort caused by dryness of the lips is typically addressed by frequent intervention of nurses or family members manually moistening the lips or giving small amounts of cool water or chipped ice. This intervention is an added burden on healthcare staff, and may not always be feasible. Various other situations can arise, particularly for infirm and sick residents and patients in nursing homes and facilities, which result in discomfort and suffering from chronic and short term conditions which result in dry or cracked lips.

Various devices have been proposed for providing short-term solutions to moisturizing the lips and/or palate under such circumstances. Examples include U.S. Pat. Nos. 4,679,551; 4,838,882; 4,917,674; 5,055,108; 5,062,795; and 6,536,423. Of these, U.S. Pat. No. 4,679,551 relates to a non-contact ultrasound spray arrangement which is complex and costly. The remaining references all relate to various devices which are positioned partly or entirely within the mouth cavity. Such devices may be somewhat effective, but are typically unpopular with patients who feel that their mouths are obstructed. In most cases, the devices extend between the lips of the patient, interfering with normal closing of the mouth and disrupting the patient's ability to resume speaking.

There is therefore a need for a simple but effective system and corresponding method for delivering moisturizing liquid to the lips of a subject suffering from dry lips without preventing closing together of the subject's lips.

SUMMARY OF THE INVENTION

The present invention is a system and corresponding method for delivering moisturizing liquid to the lips of a subject suffering from dry lips.

According to the teachings of the present invention there is provided, a method for delivering moisturizing liquid to the lips of a subject, the method comprising the steps of: (a) providing an applicator for applying the moisturizing liquid to the lips of the subject; and (b) employing a support structure to support the applicator so that at least a part of the applicator is deployed to engage a recess between the lips of the subject without obstructing contact between the upper and lower lips of the subject.

According to a further feature of the present invention, the support structure is supported primarily by at least one part of the body of the subject.

According to a further feature of the present invention, the support structure is supported at least in part by contact with the cheeks of the subject.

According to a further feature of the present invention, the support structure is supported at least in part by engagement with features of at least one ear of the subject.

According to a further feature of the present invention, the support structure includes a clamp for clamping the support structure to a bed.

According to a further feature of the present invention, the support structure includes a base configured to be self-supporting when placed on a flat surface.

According to a further feature of the present invention, the applicator includes an absorbent material moistened by the moisturizing liquid.

According to a further feature of the present invention, the applicator includes a conduit with a plurality of liquid release apertures.

According to a further feature of the present invention, there is also provided a liquid supply arrangement including: (a) a reservoir for containing a quantity of the moisturizing liquid; (b) a supply arrangement in fluid communication with the reservoir and the applicator for supplying the moisturizing liquid to the applicator.

According to a further feature of the present invention, the liquid supply arrangement is a gravity-fed liquid supply arrangement.

According to a further feature of the present invention, the reservoir maintains the moisturizing liquid at a pressure above atmospheric pressure, the pressure generating liquid flow to the applicator.

According to a further feature of the present invention, the reservoir is pressurized by the weight of a part of the subject's body resting on the reservoir, thereby feeding the moisturizing liquid to the applicator.

According to a further feature of the present invention, the applicator includes a reservoir for containing a quantity of the moisturizing liquid.

There is also provided according to the teachings of the present invention, a system for delivering moisturizing liquid to the lips of a subject, the system comprising: (a) a reservoir for containing a quantity of the moisturizing liquid; (b) an applicator for applying the moisturizing liquid to the lips of the subject; (c) a supply arrangement in fluid communication with the reservoir and the applicator for supplying the moisturizing liquid to the applicator; and (d) a support structure configured for supporting the applicator, wherein the support structure is configured to support the applicator relative to a part of the body of the subject so that at least a part of the applicator is deployed to engage a recess between the lips of the subject without obstructing contact between the upper and lower lips of the subject.

There is also provided according to the teachings of the present invention, a system for delivering moisturizing liquid to the lips of a subject, the system comprising: (a) a reservoir for containing a quantity of the moisturizing liquid; (b) an applicator for applying the moisturizing liquid to the lips of the subject; (c) a supply arrangement in fluid communication with the reservoir and the applicator for supplying the moisturizing liquid to the applicator; and (d) a support structure configured for supporting the applicator, wherein the applicator is configured for dispensing the moisturizing liquid onto the lips through contact with the lips without insertion of the applicator into the mouth of the subject.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a system and corresponding method for delivering moisturizing liquid to the lips of a subject suffering from dry lips.

The principles and operation of systems and methods according to the present invention may be better understood with reference to the drawings and the accompanying description.

Figures 1, 2, 3A, 3B:
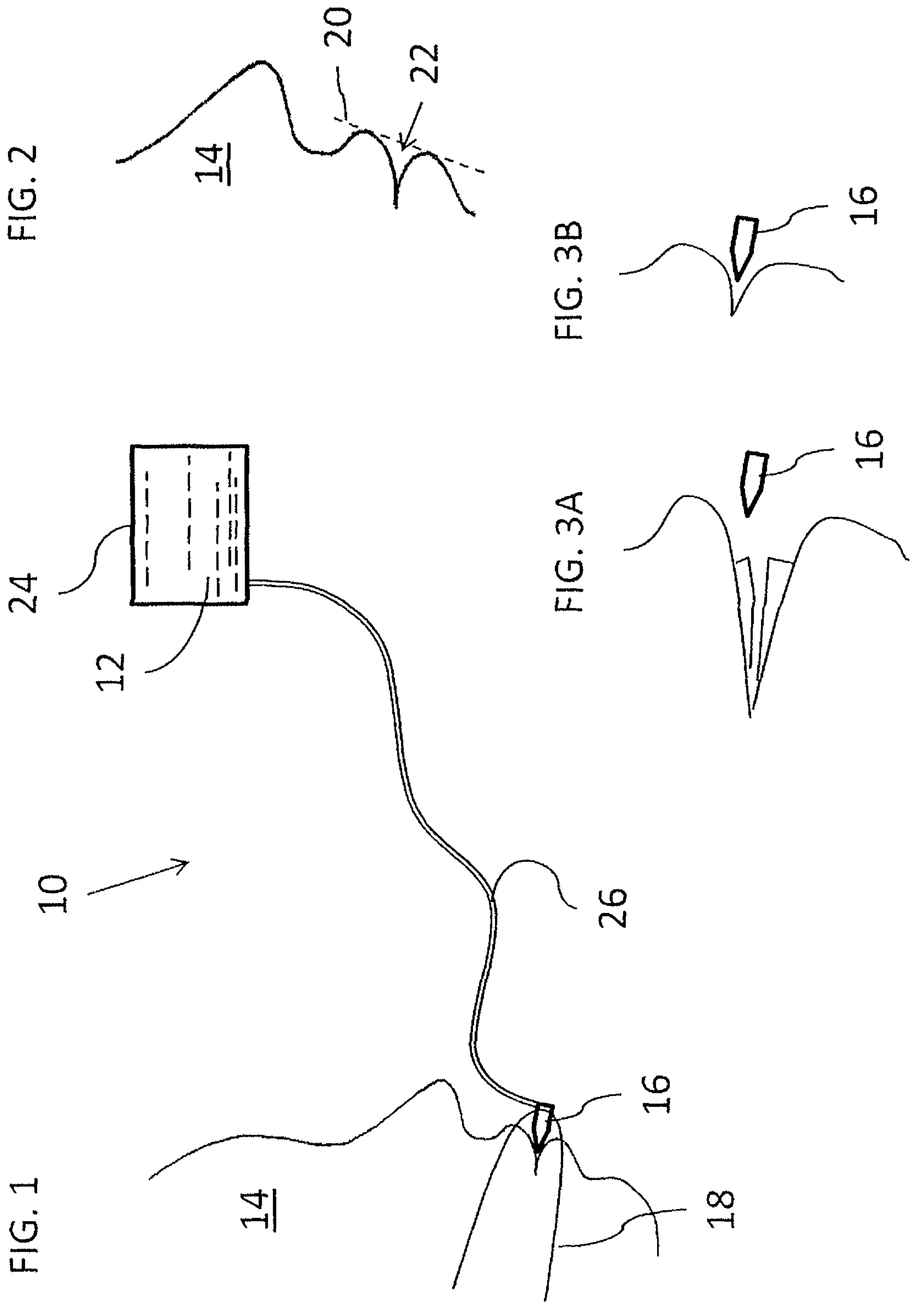
FIG. 1 is a schematic representation of a system and corresponding method according to the teachings of the present invention for delivering moisturizing liquid to the lips of a subject suffering from dry lips.
FIG. 2 is a schematic side view of the face of a subject illustrating graphically the region referred to herein as a "recess between the lips of the subject"
FIGS. 3A and 3B are partial side views of the face of FIG. 2 with the mouth open and closed, respectively, illustrating a preferred positioning of an applicator engaging a recess between the lips of the subject without obstructing contact between the upper and lower lips.

Referring now to the drawings, FIG. 1 illustrates schematically a system, generally designated 10, and a corresponding method according to the teachings of the present invention for delivering moisturizing liquid 12 to the lips of a subject 14. In general terms, system 10 includes an applicator 16 for applying the moisturizing liquid to the lips of the subject, and a support structure 18. Support structure 18 is arranged to support applicator 16 so that at least a part of applicator 16 is deployed so as to engage a recess between the lips of subject 14 without obstructing contact between the subject's upper and lower lips.

It will be noted that the positioning of applicator 16 as described herein, engaging the recess between the lips but without obstructing closure of the lips together, is highly advantageous. On one hand, the proximity of applicator 16 to the lips allows the use of simple contact-based implementations of applicator 16, thereby providing continuous and mess-free relief to the discomfort of the subject without requiring complex or expensive applicator devices. At the same time, by avoiding any obstruction to contact between the lips, disruption of speech and other normal oral movement is avoided, thereby making the system as non-intrusive as possible. These and other advantages of the systems and methods of the present invention will become clearer from the following detailed description.

Before addressing the features of the present invention in more detail, it will be helpful to define certain terminology as used herein in the description and claims. Firstly, the term "recess" is used herein in the description and claims to refer to a geometrical form in two dimensions, corresponding to the outline of a body part, which can be closed by addition of a single straight line to enclose an area. This definition is represented graphically in FIG. 2 in which the outline of the face 14, taken in side view (or cross-section) exhibits a recess between the lips, while the lips are closed together, which can be closed in geometrically by addition of a single straight line, as illustrated by dashed line 20. The area 22 enclosed by the body part together with the straight line is referred to as "within the recess". An object located at least partially within the recess is referred to as "engaging the recess", without necessarily requiring it to be in contact with sides of the recess continuously. In all of the above terminology, it will be noted that the definitions refer to geometrical relations in two dimensions only, and particularly relating to an outline as viewed in a cross-section in the sagittal plane with the mouth closed. Clearly, the geometry of the human mouth is somewhat convexly curved in the side-to-side direction, and the recess referred to above may be an open-ended channel in three dimensions, or may otherwise change towards its lateral edges.

When reference is made to an applicator being positioned such that is does not "obstruct contact between the subject's upper and lower lips," this used to indicate that the lips are free to contact each other directly across the entire width of the mouth without any intervening object or material. This terminology thus excludes all types of devices which have portions extending into the mouth, or which are mounted in various manners to the lips or teeth.

Turning now to the remaining features of the schematic representation of system 10 illustrated in FIG. 1, the various implementations of the present invention preferably include a reservoir 24 for containing a quantity of moisturizing liquid 12, and a supply arrangement, illustrated here as a fluid flow conduit 26, in fluid communication with reservoir 24 and applicator 16 for supplying moisturizing liquid 12 to applicator 16.

Liquid 12 itself may be any non-toxic liquid effective for moistening the lips. The liquid is typically water-based, and may have additives to provide a sweet taste or any other desired flavor, additives to improve efficacy for treatment of dry lips or any other desired additives. Where additives are present, they may be in the form of a solution, a suspension, an emulsion or any other form. Most preferably, plain water is used. In certain cases, particularly where the subject is at risk of infection, sterilized water may be used. In many cases, regular drinking water may be sufficient.

FIGS. 3A and 3B show an enlarged view of applicator 16 deployed in engagement with the recess between the lips of a subject while the subject's mouth is open and closed, respectively. As seen here, applicator 16 is preferably kept in proximity to the lips during movement of the mouth, but does not obstruct normal opening and closing movement of the mouth, or any other motion of the mouth normally required for speech or facial expression.

Turning now to FIGS. 4-11B, it should be noted that system 10 as described schematically with reference to FIGS. 1-3B above may be implemented in a large number of practical implementations. More specifically, while maintaining the common functional features described thus far, each of applicator 16, support structure 18, reservoir 24 and supply arrangement 26 may be implemented in numerous ways. In order to give some indication of the scope of possible implementations, system 10 will be further illustrated with reference to seven non-limiting exemplary embodiments. The first three of these employ support structures 18 which are configured to be supported primarily by at least one part of the body of the subject, and most preferably, part of the head of the subject, thereby maintaining the desired position relative to the lips of the subject even if the subject moves around considerably. The latter four embodiments employ various support structures 18 which cooperate with the frame or other surfaces of a bed, an intravenous drip stand or other nearby furniture. It should be noted that, unless otherwise indicated, the various implementations of each component of system 10 may be used interchangeably between the embodiments, and are not limited to the specific combinations illustrated here.

Figure 4B:
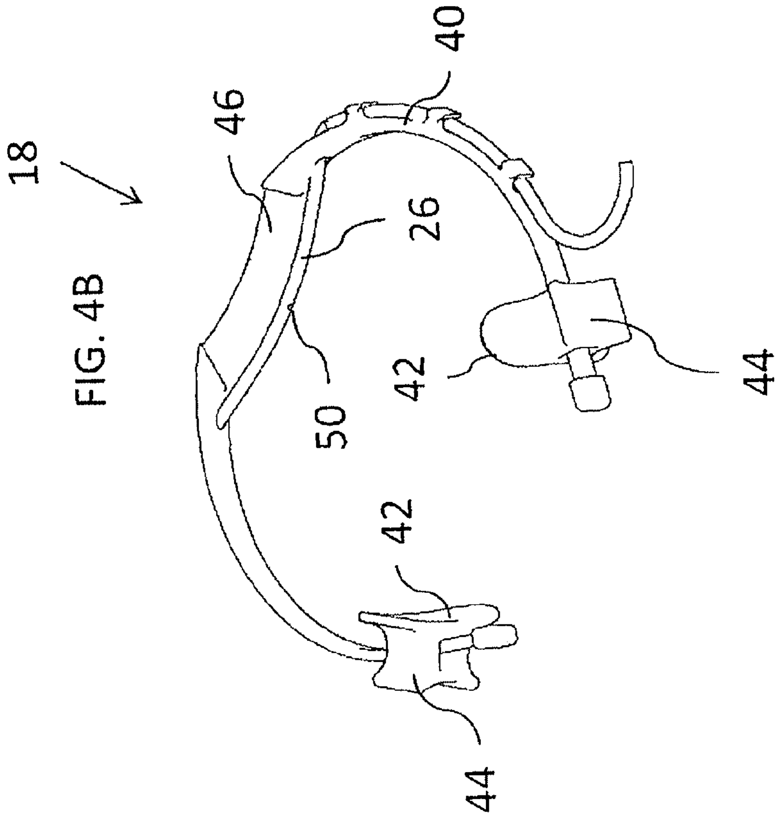
FIG. 4B is a view similar to FIG. 4A with an absorbent element of the applicator removed.
Figure 4A:
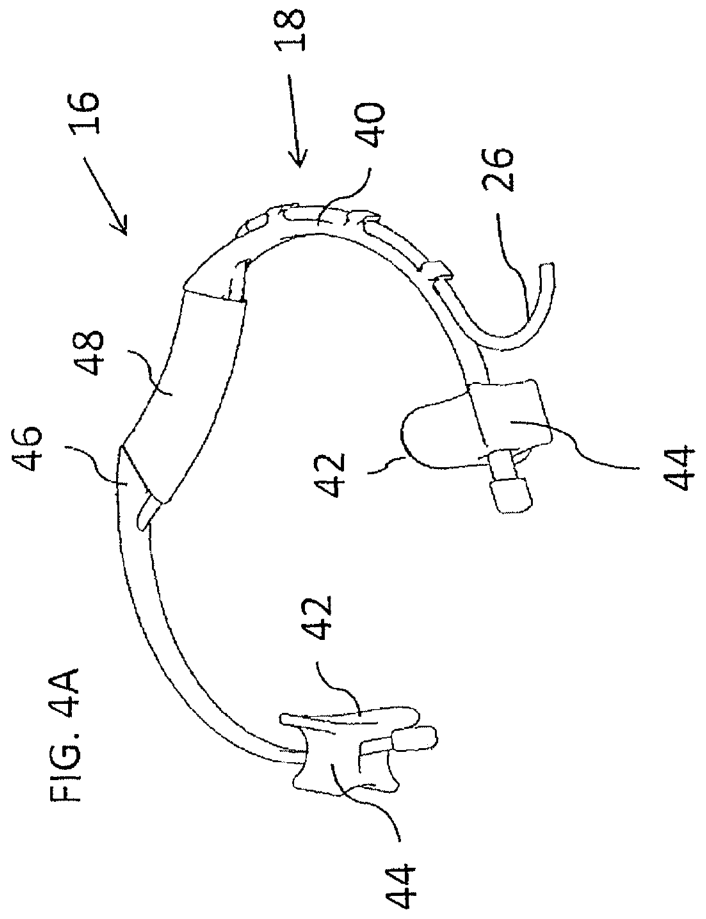
FIG. 4A is an isometric view of an applicator and support structure, constructed and operative according to the teachings of the present invention, for implementing a first preferred embodiment of the system of FIG. 1.
Figure 5:
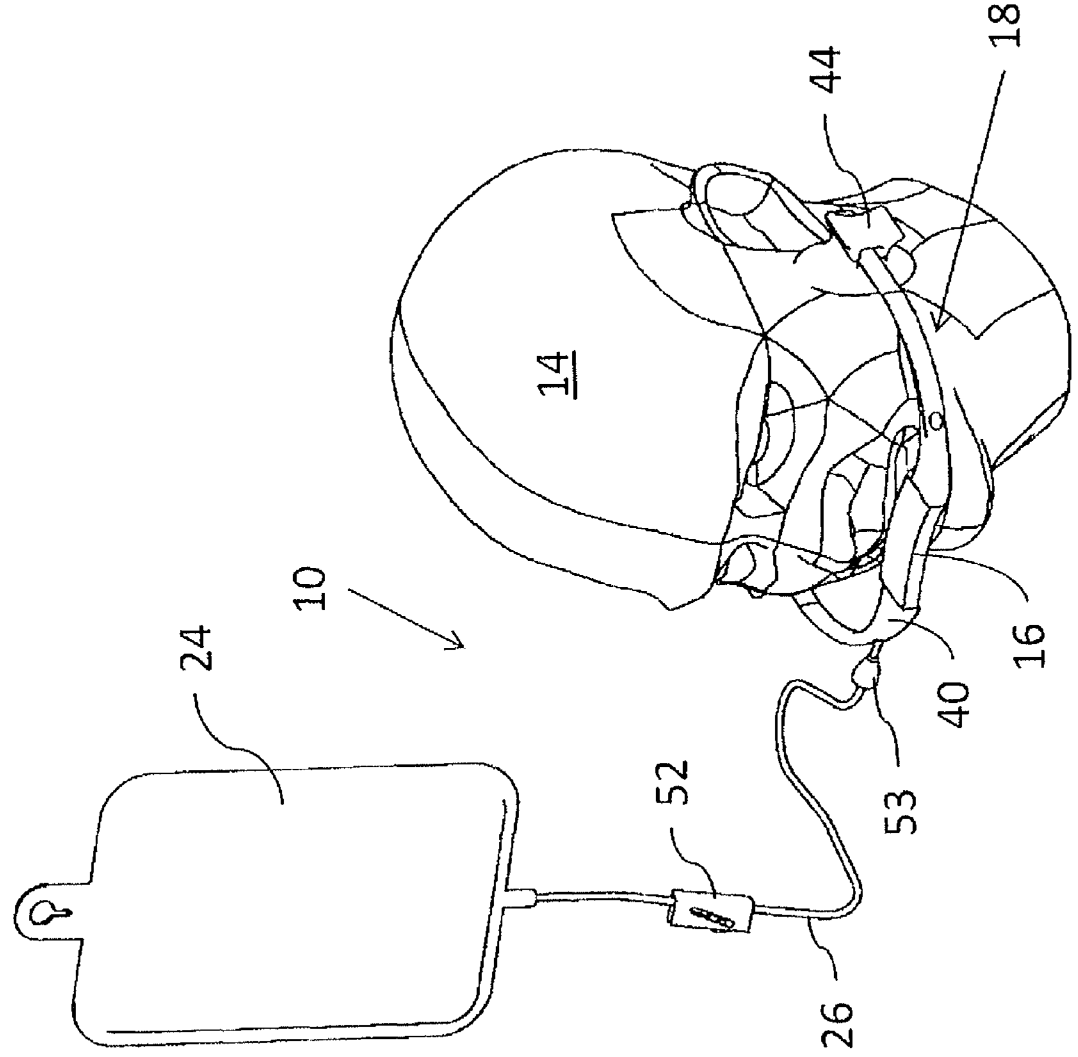
FIG. 5 is an isometric view of a first preferred embodiment of the system of FIG. 1 employing the applicator and support structure of FIG. 4A.

Turning specifically to FIGS. 4A, 4B and 5, this illustrates a first embodiment of system 10 wherein support structure 18 is primarily supported by contact with the cheeks of subject 14. In this case, support structure 18 is formed as a resilient frame 40, shown here with a roughly arcuate shape, with cheek contact regions 42 provided by grip elements 44. Grip elements 44 are preferably formed from relatively soft resilient material, such as natural or synthetic rubber or silicone, which provide firm but comfortable grip on the cheeks of the subject. Grip elements 44 may be slidably mounted on the arms of frame 40 to provide adjustment of the size of the subject. Frame 40 is typically formed from low-cost injection-molded plastic.

A central portion of frame 40 preferably includes a flattened region 46 which protrudes inwardly, forming a convex contour which contrasts with the generally concave curvature of the inside of the arcuate shape. This portion provides support for, and defines the shape of, the applicator 16 of this embodiment, as will now be described.

Applicator 16 in this embodiment includes an absorbent material moistened by liquid 12 which serves to disperse the liquid over a desired contact area through capillary action. Liquid 12 is applied to the lips as they come into contact with the moistened absorbent material. In the preferred case illustrated here (FIG. 4A), the absorbent material is implemented as a layer 48 of woven or non-woven cloth or open-cell foam material wrapped around flattened region 46 of frame 40.

Supply of liquid 12 to layer 48 occurs via fluid flow conduit 26 which has one or more liquid release aperture 50, as revealed in FIG. 4B. Parenthetically, it should be noted that a structure such as shown in FIG. 4B, without absorbent material, may be used directly as an applicator, optionally provided with a plurality of openings to distribute the liquid more evenly across the lips. Conduit 26 as shown here passes along one side of frame 40, typically held in place by a number of clips integrally formed with the frame, and extends around the inward-facing edge of flattened region 46 where aperture 50 is located. In this manner, fluid supply is ensured primarily to the absorbent material on the side of flattened region 46 facing the lips. In the case shown here, conduit 26 passes through a lateral opening formed in frame 40 so as to pass neatly from the outside to the inside of the arcuate frame.

FIG. 5 illustrates the system in use with grip elements 44 gripping the subject's cheeks and applicator 16 engaged in the recess between the lips of the subject, but without obstructing contact between the lips.

The device of FIGS. 4A-4B may be used to advantage with substantially any form of reservoir 24 and liquid supply arrangement. In the example illustrated in FIG. 5, a gravity-fed liquid supply arrangement with a suspended flexible reservoir "bag" of a type familiar from intravenous drip ("I.V.") arrangements is shown. A simple flow regulating control 52, also of a type commonly used in I.V. sets, may be used to limit the flow rate to a suitable flow rate. Additionally, or alternatively, this and other embodiments of the present invention may include a flow limiting element 53 incorporated within conduit 26, or at any other point along the flow path, to limit the flow rate to a suitable level. Suitable flow rate limiting elements may be implemented using well developed technology (e.g., flow labyrinths or pressure-regulating diaphragms) common in drip irrigation systems which provide a desired flow rate largely independent of variations in the supply pressure.

According to one particular example of a flow limiting element, a capillary tube is incorporated within the flow path. Preferably, the capillary tube has an internal diameter of between about 0.05 mm and about 0.2 mm, and most preferably about 0.1±0.03 mm. To facilitate attachment of the capillary tube, and external diameter of about 3 mm has been found convenient. A length of the capillary is preferably between about 5 and about 30 mm, and most preferably about 8±3 mm. Such a capillary can conveniently be attached at the end of conduit 26 or otherwise be deployed to define an outlet to applicator 16. In experiments performed by the applicant, a glass capillary tube of internal diameter 0.1 mm and length 8 mm has been found effective when used with an infusion bag supply positioned 70-110 cm above the outlet to maintain flow rates of around 10 cc. per hour.

Figure 6:
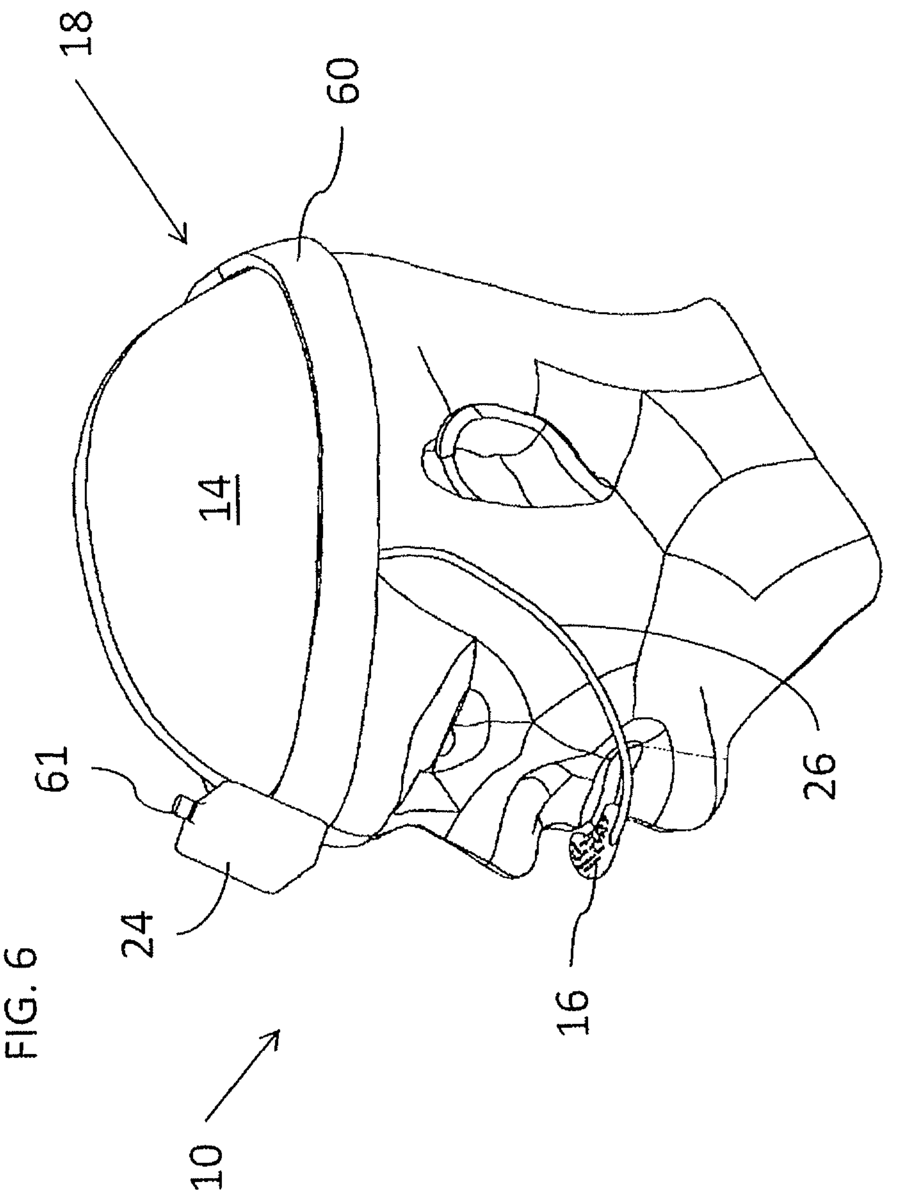
FIG. 6 is an isometric view of a second preferred embodiment of the system of FIG. 1.

Turning now to FIG. 6, there is shown an alternative embodiment of system 10, in this case employing a support structure 18 which suspends applicator 16 from a hat or head-band 60 substantially encircling the crown of the subject 14. In the case illustrated here, reservoir 24 is shown mounted directly on head-band 60. Optionally, reservoir 24 may have an opening 61 for convenient refilling of reservoir 24. Applicator 16 may be suspended from head-band 60 via any suitable suspension arrangement. Preferably, one or more stiff arm is used to retain the applicator in place. Optionally, the arm may be deformable in order to allow repositioning of the applicator in the correct position for the subject. According to a particularly preferred option illustrated here, conduit 26 may itself be implemented as a tube sufficiently stiff to provide the repositionable deployment as described.

Applicator 16 as illustrated here is a hollow body, typically of plastic, with an array of small openings for releasing liquid. The size of the openings, as well as coatings or other surface properties of the applicator, may be chosen to provide drip-free retention of liquid at the openings through surface tension effects. Liquid is then released by contact against the lips of the subject.

Figures 7A, 7B:
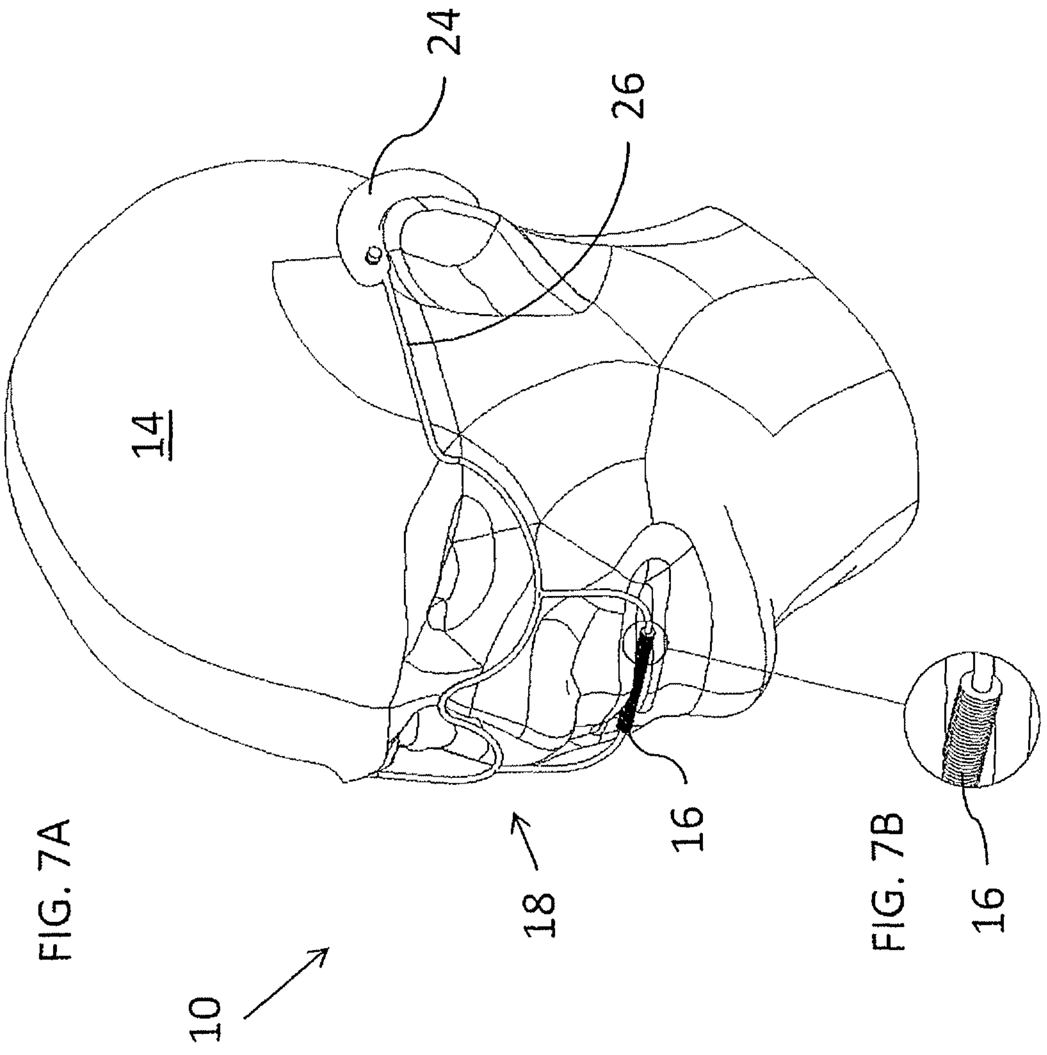
FIG. 7A is an isometric view of a third preferred embodiment of the system of FIG. 1.
FIG. 7B is an enlarged view of the circled portion of FIG. 7A as shown.

Turning now to FIGS. 7A and 7B, this illustrated a further alternative embodiment of system 10 in which support structure 18 is implemented with an eye-glasses-type support frame which engages at least one and preferably both ears of the subject 14. In the version shown here, support structure 18 also features a bridge portion lying across the bridge of the subject's nose. These features together provide a well defined support geometry, allowing precise positioning of applicator 16 within the recess between the lips of the subject.

One attractive option for this implementation is positioning reservoir 24 over and/or behind the ears. In order to ensure comfortable balance between the two sides, it may be preferably to provide two similar reservoirs on opposite sides of the support structure, one resting on each ear. flow conduit(s) 26 are preferably implemented as part of support structure 18, or as thin tubes passing within the structure. Flow from reservoirs 24 to applicator 16 is preferably achieved through capillary action drawing water through the fine tubes of support structure 18 to applicator 16.

Applicator 16 as shown here, best seen in FIG. 7B, is implemented in a manner conceptually similar to that of FIG. 4A, with an absorbent material deployed around a tube with drop release apertures.

Figure 8B:
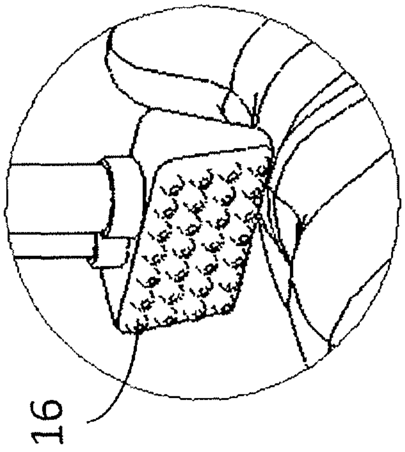
FIG. 8B is an enlarged view of the circled portion of FIG. 8A designated "A"
Figure 8A:
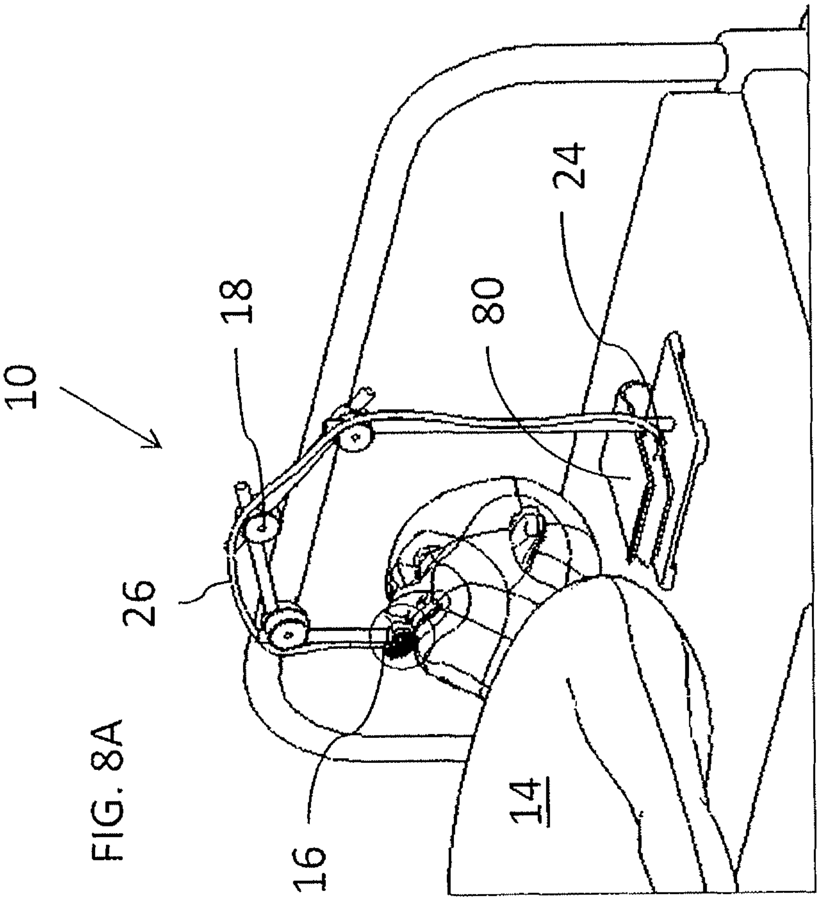
FIG. 8A is an isometric view of a fourth preferred embodiment of the system of FIG. 1.

Turning now to FIGS. 8A and 8B, there is shown an implementation of system 10 in which support structure 18 is an adjustable jointed stand with a base configured to be self-supporting when placed on a flat surface, such as the surface of a bed. This allows positioning of applicator 16 in an appropriate position for short term use by a subject confined to bed, such as for example while recovering from anesthesia. Applicator 16, shown more clearly in FIG. 8B, is similar to that of FIG. 6.

A reservoir 24 is here provided at or near the base of stand 18, and is connected to applicator 16 via a conduit 26. A driving force for supplying liquid to applicator 16 is provided by a spring-clamp 80 applied so as to apply pressure to external surfaces of flexible reservoir 24. The pressure of the spring-clamp maintains moisturizing liquid 12 within reservoir 24 at a pressure above atmospheric pressure, thereby generating liquid flow to the applicator.

Figure 9B:
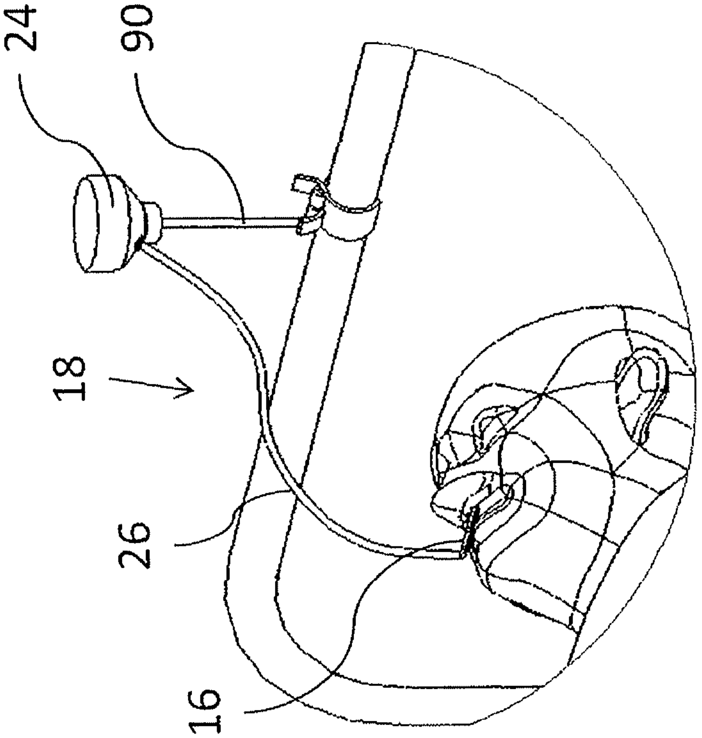
FIG. 9B is an enlarged view of the circled portion of FIG. 9A designated "A"
Figure 9A:
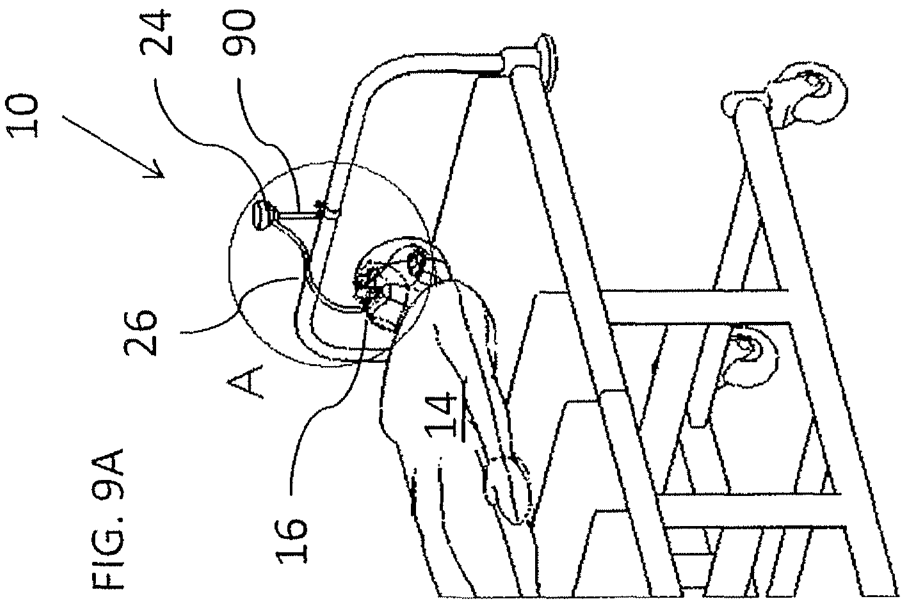
FIG. 9A is an isometric view of a fifth preferred embodiment of the system of FIG. 1.

Turning now to FIGS. 9A and 9B, these show a further variant embodiment based on a raised reservoir 24 mounted on a bracket 90 which holds it at a level above the subject by clamping to part of a bed frame. Applicator 16 is here shown as a tube with a number of apertures formed at the end of a semi-rigid conduit 26 connecting applicator 16 to reservoir 14.

Figure 10A:
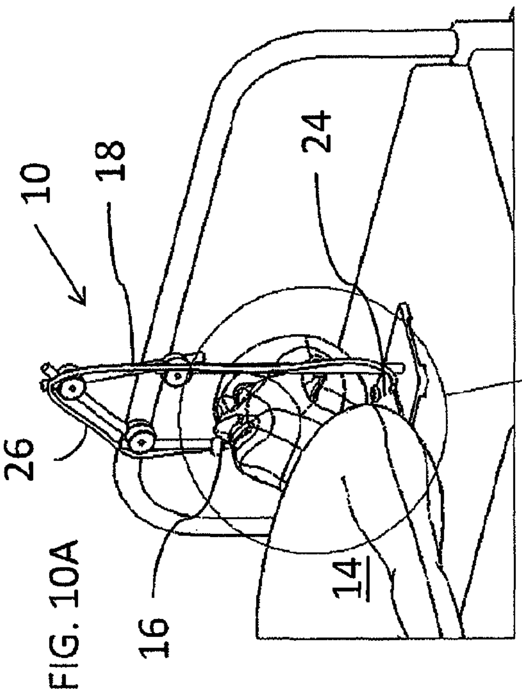
FIG. 10A is an isometric view of a sixth preferred embodiment of the system of FIG. 1.
Figure 10B:
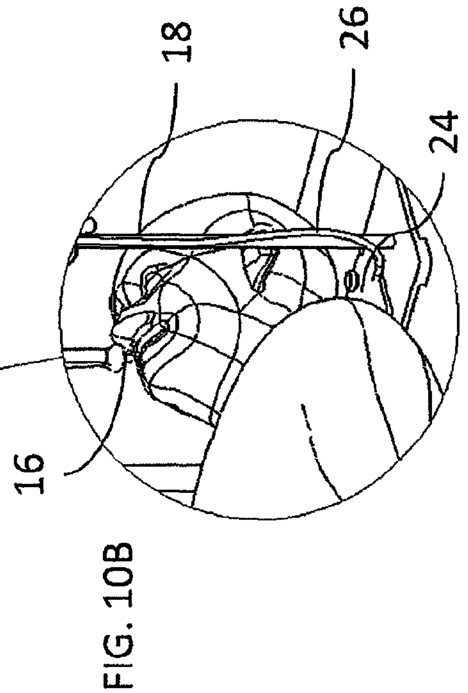
FIG. 10B is an enlarged view of the circled portion of FIG. 10A as shown.

FIGS. 10A and 10B illustrate an implementation generally similar to that of FIGS. 8A and 8B, but in which reservoir 24 is pressurized by the weight of a part of the subject's body, in this case the head, resting on reservoir 24, thereby feeding the moisturizing liquid to applicator 16. Most preferably, reservoir 24 may be located within or under a pillow to be used by the subject. Applicator 16 itself is shown here as a single drop emitter mounted at the end of conduit 26.

Figure 11A:
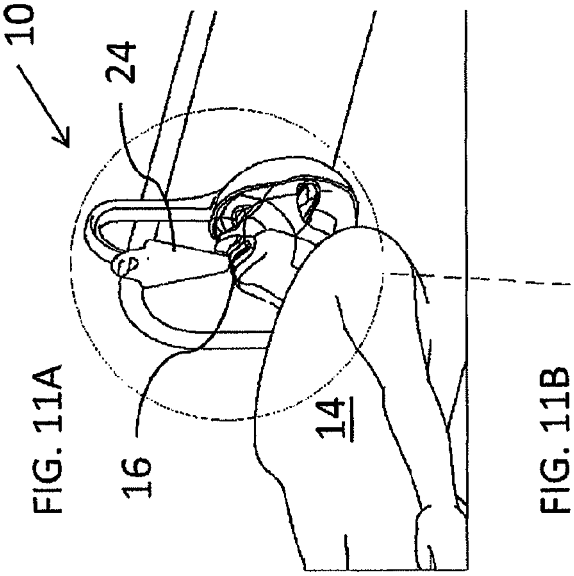
FIG. 11A is an isometric view of a seventh preferred embodiment of the system of FIG. 1.
Figure 11B:
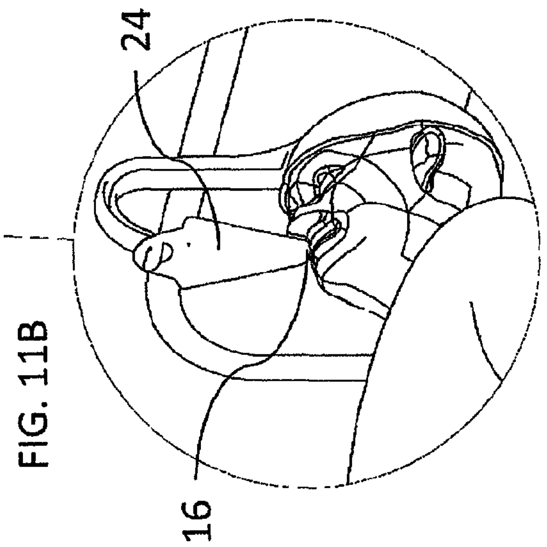
FIG. 11B is an enlarged view of the circled portion of FIG. 11A as shown.

Turning finally to FIGS. 11A and 11B, it should be noted that not all embodiments necessarily require a distinct conduit 26 connecting between reservoir 24 and applicator 16 as shown in the previous embodiments. Instead, in this embodiment, reservoir 24 is formed as an integrated part of applicator 16. The device is thus essentially a hanging reservoir 24 with an applicator 16 formed in its lower portion. The device is hung from a suitable stand, thereby achieving the desired positioning of the applicator 16 in the recess between the lips of the subject without obstructing contact between the lips.

Once again, it should be stressed that the various implementations of different elements of system 10 shown herein are not limited to the particular combinations illustrated. Thus, for example, the embodiments of FIGS. 4A, 4B and 5 may be implemented using a head mounted reservoir such as was shown in FIG. 6, or various other gravity-fed, pre-pressurized or body-weight pressurized reservoir arrangements. A manually-operable supply (e.g., a squeezable reservoir or a small manually-operable pump such as is common in liquid soap dispensers) also falls within the scope of the present invention.

It will be appreciated that the above descriptions are intended only to serve as examples, and that many other embodiments are possible within the scope of the present invention as defined in the appended claims.

What is claimed is:

1. A method for delivering moisturizing liquid to the lips of a subject, the method comprising the steps of:

(a) providing an applicator including an absorbent material moistened by a moisturizing liquid configured for contact application of the moisturizing liquid to an upper and lower lip of the subject; and (b) employing a support structure to support said applicator so that at least a part of said applicator is deployed to engage a recess between the an upper and lower lip of the subject without any part of said applicator obstructing contact between the upper and lower lip of the subject.

2. The method of claim 1, wherein said support structure is configured to be supported primarily by at least one part of the body of the subject.

3. The method of claim 1, wherein said support structure is configured to be supported at least in part by contact with the cheeks of the subject.

4. The method of claim 1, wherein said support structure is configured to be supported at least in part by engagement with features of at least one ear of the subject.

5. The method of claim 1, wherein said support structure includes a clamp for clamping said support structure to a bed.

6. The method of claim 1, wherein said support structure includes a base configured to be self-supporting when placed on a flat surface.

7. The method of claim 1, wherein said applicator includes a conduit with a plurality of liquid release apertures deployed to release the moisturizing liquid to moisten said absorbent material.

8. The method of claim 1, further comprising providing a liquid supply arrangement including:

(a) a reservoir for containing a quantity of the moisturizing liquid;

(b) a supply arrangement in fluid communication with said reservoir and said applicator for supplying the moisturizing liquid to said applicator.

9. The method of claim 8, wherein said liquid supply arrangement is a gravity-fed liquid supply arrangement.

10. The method of claim 8, wherein said reservoir maintains the moisturizing liquid at a pressure above atmospheric pressure, said pressure generating liquid flow to said applicator.

11. The method of claim 8, wherein said reservoir is configured to be pressurized by the weight of a part of the subject's body resting on said reservoir, thereby feeding the moisturizing liquid to said applicator.

12. The method of claim 1, wherein said applicator includes a reservoir for containing a quantity of the moisturizing liquid.

13. The method of claim 1, wherein said applicator includes a flow restriction comprising a length of capillary tube having an internal diameter no greater than 0.2 mm.

14. A system for delivering moisturizing liquid to the lips of a subject, the system comprising:

(a) a reservoir for containing a quantity of a moisturizing liquid;

(b) an applicator including an absorbent material moistened by the moisturizing liquid configured for contact application of the moisturizing liquid to an upper and lower lip of the subject;

(c) a supply arrangement in fluid communication with said reservoir and said applicator for supplying the moisturizing liquid to said applicator; and (d) a support structure configured for supporting said applicator, wherein said support structure is configured to support said applicator relative to a part of the body of the subject so that at least a part of said applicator is deployed to engage a recess between the upper and lower lip of the subject without any part of said applicator obstructing contact between the upper and lower lip of the subject.

15. The system of claim 14, wherein said supply arrangement includes a flow restriction comprising a length of capillary tube having an internal diameter no greater than 0.2 mm.

16. A system for delivering moisturizing liquid to the lips of a subject, the system comprising:

(a) a reservoir for containing a quantity of a moisturizing liquid;

(b) an applicator configured for applying the moisturizing liquid to lips of a subject;

(c) a supply arrangement in fluid communication with said reservoir and said applicator for supplying the moisturizing liquid to said applicator; and (d) a support structure configured for supporting said applicator, wherein said applicator includes an absorbent material moistened by the moisturizing liquid configured for dispensing the moisturizing liquid onto the lips through contact with the lips without insertion of any part of said applicator into the mouth of the subject.

17. The system of claim 16, wherein said supply arrangement includes a flow restriction comprising a length of capillary tube having an internal diameter no greater than 0.2 mm.

* * * * *